United States Patent
Uzgiris et al.

(10) Patent No.: US 6,470,204 B1
(45) Date of Patent: Oct. 22, 2002

(54) INTRACAVITY PROBE FOR MR IMAGE GUIDED BIOPSY AND DELIVERY OF THERAPY

(76) Inventors: Egidijus Edward Uzgiris, 1206 Viewmoant Dr., Schenectady, NY (US) 12309; Kenneth William Rohling, 13 Skaarland Dr., Burnt Hills, NY (US) 12027; Ronald Dean Watkins, 1584 Clifton Park Rd., Niskayuna, NY (US) 12309; Robert David Darrow, 71 Spring Rd., Scotia, NY (US) 12302; Charles Lucian Dumoulin, 36 Terrace Ct., Ballston Lake, NY (US) 12019; Randy Otto John Giaquinto, 20 Kelly Meadow Rd., Burnt Hills, NY (US) 12027; Michael Edward Moran, 103 Blockhouse Creek Ct., Albany, NY (US) 12203

( * ) Notice: Subject to any disclaimer, the term of this patent is extended or adjusted under 35 U.S.C. 154(b) by 96 days.

(21) Appl. No.: 09/609,899

(22) Filed: Jul. 3, 2000

Related U.S. Application Data

(60) Provisional application No. 60/150,640, filed on Aug. 25, 1999.

(51) Int. Cl.[7] ................................................ A61B 5/05
(52) U.S. Cl. ........................ 600/411; 600/417; 600/424; 606/130
(58) Field of Search .................................. 600/411, 407, 600/410, 417, 422, 423, 424, 587–594; 324/318, 322, 309; 606/130

(56) References Cited

U.S. PATENT DOCUMENTS

| | | | | | |
|---|---|---|---|---|---|
| 5,304,214 | A | * | 4/1994 | DeFord et al. | 604/916 |
| 5,471,988 | A | * | 12/1995 | Fujio et al. | 600/439 |
| 6,304,769 | B1 | * | 10/2001 | Arenson et al. | 600/424 |
| 6,320,379 | B1 | * | 11/2001 | Young | 324/309 |
| 6,327,492 | B1 | * | 12/2001 | Lemelson | 600/434 |

* cited by examiner

Primary Examiner—Marvin M. Lateef
Assistant Examiner—Jeoyuh Lin
(74) Attorney, Agent, or Firm—Jean K. Testa; Jill M. Breedlove

(57) ABSTRACT

An insertable intracavity probe for use in Magnetic Resonance Imaging (MRI) and therapy of a region of interest proximal to a cavity, the probe having a substantially rigid probe shell for insertion into the cavity. The probe shell is adapted to incorporate at least one device for imaging the region of interest. A guide track is incorporated in the probe shell and is adapted to guide at least one biopsy or therapy device to the region of interest during imaging. Intracavity regions include cervical, rectal, and other regions associated with internal cavities of a patient.

15 Claims, 7 Drawing Sheets

INTRACAVITY PROBE FOR MR IMAGE GUIDED BIOPSY AND DELIVERY OF THERAPY

CROSS REFERENCE TO RELATED APPLICATIONS

This application is related to Provisional Application U.S. Ser. No. 60/150,640, filed Aug. 25, 1999 in the U.S. Patent and Trademark Office, the contents of which are incorporated herein by reference, and the benefit of priority to which is claimed under 35 U.S.C. 119(e).

STATEMENT REGARDING FEDERALLY SPONSORED RESEARCH & DEVELOPMENT

The US Government may have certain rights in this invention pursuant to contract number DAMD17-99-1-9008 awarded by the United States Army.

BACKGROUND OF THE INVENTION

The present invention relates generally to magnetic resonance imaging (MRI) and intracavity probes used in MRI, and, more particularly, to MRI probes for MRI guided biopsy and delivery of therapy of the prostate.

Prostate cancer is the second leading cause of cancer death among men. Due to the non-specificity of prostate specific antigen (PSA) screening, in which a high level of PSA signifies a possible tumor problem but is also associated with benign prostate hyperplasia and prostatitis, many biopsy procedures must be undertaken to confirm a diagnosis in accordance with high PSA levels. In particular, no surgical or radiation therapy can proceed without a positive biopsy result.

Ultrasound imaging does not visualize lesions very well in the prostate and, as a result, the biopsy procedures are taken in a random fashion over the several sectors of the prostate. The ultrasound imaging is used to locate the prostate and guide the biopsy needles to specific locations in the sampling pattern, which may involve up to 6 or 8 biopsy samples. A positive biopsy finding would prompt further treatment or therapy, under current medical procedures. However, a negative biopsy does not necessarily mean the patient is free of cancer, since the sampling procedures may not find suspect tissue.

Ultrasound guided biopsy of the prostate is a common procedure. The ultrasound is used to image the prostate in real time. Because of a fixed geometry between the ultrasound crystal and the needle guide, it is possible to project the location of the biopsy volume directly on the image screen as the probe is moved and manipulated. Ultrasound guided biopsy probes are cylindrical in shape and not larger in diameter than 2.5 cm. This diameter is at the limit of acceptability to some 95% of patients . . . for the other 5% the probe diameter is too large and there is sufficient discomfort for the procedure to be stopped. Such a probe design is possible for MR applications but is not optimal for coil placement close to the rectum.

MR imaging with an internal surface coil, the endorectal coil, which is inserted into the rectum, gives very good images of the prostate and of the cancer lesions. MR imaging provides the ability for accurate and real-time localization of suspected lesions. Thus, acquiring images by MR imaging for guiding biopsy needles would reduce the number of biopsy samples, and the random sampling procedure could be eliminated given the ability to localize suspected lesions.

A current probe design for acquiring MR images is the commercially available endorectal coil for MR, which is a flexible coil that is expanded inside the rectum by a balloon. However, it is not suitable for delivery of biopsy needles or of therapy devices as there is no firm base from which to reference position of the interventional devices.

For MR guided prostate biopsy or prostate therapy, a number of requirements need to be met which are unique to the combination of MR detection and the capabilities of therapy and/or biopsy devices in one probe. In order to obtain high resolution MR images, it is desirable that a receive coil is incorporated into the probe and that this coil be placed as close as possible to the prostate. The coil location is desirably in close proximity to the rectum because the signal sensitivity of a small receive coil falls off sharply with distance. By necessity, for purposes of patient comfort, the receive coil width is desirably no larger than about 2.5 cm. Another requirement is that the device be easily manipulated inside the rectum to be able to sample the entire prostate for biopsy purposes or for the application of therapy. Thus, all sectors of the prostate are desirably accessible. The device is desirably substantially rigid to provide a firm base for biopsy needle guides or for ultrasound crystals. The device is desirably of sufficient size to physically incorporate the needle guides or crystals. Finally to locate the image plane precisely and follow it as the probe is moved or as the patient moves, a set of Magnetic Resonance (MR) tracking coils are incorporated as well. These requirements pose a challenge for the design of an appropriate probe.

What is needed is a probe configuration for MR imaging an intracavity region of interest proximal to the cavity, such as the prostate. Further needed is a probe configuration that allows access to all areas of the prostate for biopsy sampling or for the introduction of therapeutic devices during MR image acquisition, in order to accurately and in real-time localize suspected tissue of the region of interest.

BRIEF SUMMARY OF THE INVENTION

An insertable intracavity probe for use in Magnetic Resonance Imaging (MRI) and therapy of a region of interest proximal to a cavity is provided. The probe comprises, a substantially rigid probe shell for insertion into the cavity. The probe shell is adapted to incorporate at least one device for imaging the region of interest, and the probe shell further being adapted to incorporate at least one therapy device, such as a biopsy device or therapy delivery device, for application on the region of interest during imaging. Further, a method for MRI guided biopsy and therapy delivery to a region of interest proximal to a cavity is provided.

BRIEF DESCRIPTION OF THE DRAWINGS

The features and advantages of the present invention will become apparent from the following description of the invention when read with the accompanying drawings in which.

DETAILED DESCRIPTION

Figure 1:
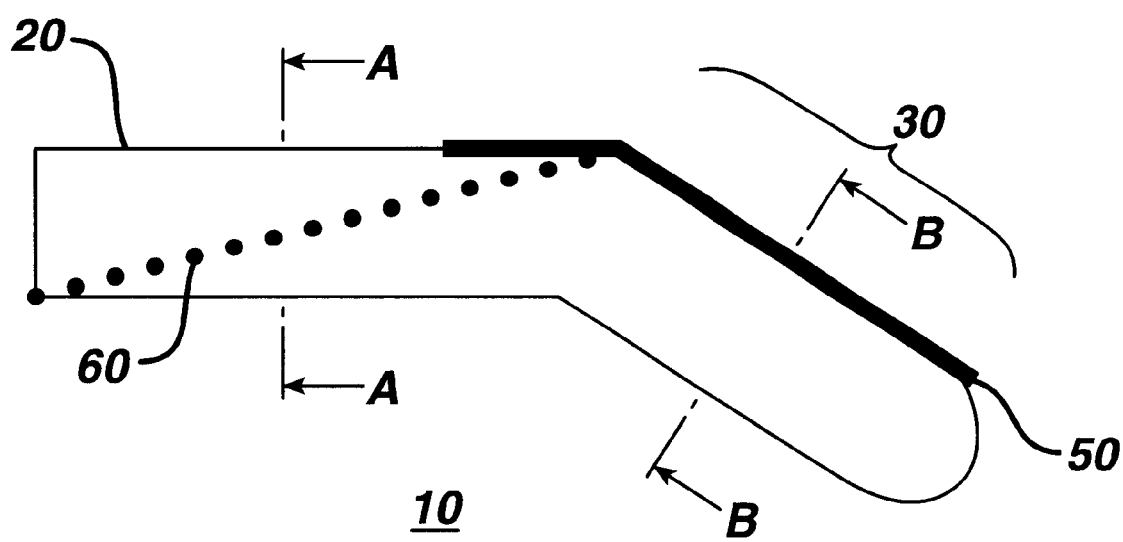
FIG. 1 illustrates an exemplary intracavity probe to which preferred embodiments of the present invention are applicable.

In FIG. 1 is shown an exemplary intracavity probe to which preferred embodiments of the present invention are applicable. The particular implementation of the intracavity probe is a Magnetic Resonance (MR) probe for the prostate and is by way of example only. That is, the invention described herein applies to other implementations for which intracavity probes for imaging are applicable, for example cervical, rectal, and other regions associated with internal cavities of a patient.

Figure 1A:
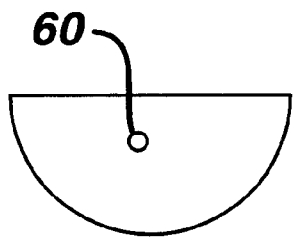
Figure 1B:
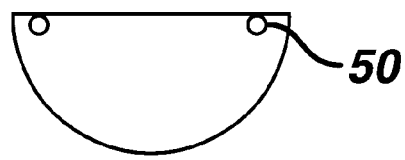

Referring to FIG. 1, an insertable intracavity probe 10 comprises a probe shell 20 for insertion into said cavity. Probe shell 20 is substantially rigid such that it does not deform within the cavity being imaged. In an embodiment, probe shell 20 is constructed of a material such as, for example, optically cured epoxy (SL-51900) or similar material such that probe shell is substantially rigid within the cavity. Probe shell 20 has an insertion end 30 and a handle end 40 (not shown, see FIG. 3) opposing the insertion end. Probe shell 20 is adapted to incorporate at least one imaging device, such as receive coil 50, for imaging a region of interest proximal to a cavity of a patient. As FIG. 1 shows, receive coil 50 is placed adjacent to the surface of probe shell. In an embodiment, receive coil 50 is adjacent to the inner surface of probe shell 20. FIG. 1B shows a cross-section view of probe shell 20 and relative placement of receive coil 50 being on an internal surface of probe shell 20. Probe shell 20 is also adapted to incorporate at least one biopsy or therapy device (not shown) for use on the region of interest. As used herein, the terms "adapted to" or "configured to" are used to refer to the ability of probe shell 20 to include components and/or features, and still enable use when the probe is inserted. In a preferred embodiment, probe shell 20 is a substantially rigid shell or casing that permits the incorporation of receive coil 50, and other devices of which descriptions follow.

Additionally, the shape of probe shell 20 allows for ease of manipulation of the probe inside the cavity, such as the rectum, to be able to sample the entire prostate for biopsy purposes or for the application of therapy. Also, various sectors of the area of interest, such as the prostate, are accessible. In an embodiment, probe shell 20 is substantially hemispherically shaped (having a flat surface and a rounded surface at a cross-section, as shown in FIGS. 1A and 1B) at the insertion end. FIG. 1 shows the hemispherical shape to be formed as half of a circular probe; the rounded surface of the probe may be formed from a circle, ellipse, or other similar configurations. Also, in this embodiment, receive coil 50 is a 20 mm by 70 mm surface coil that is placed adjacent to the flat surface of the substantially hemispherically shaped probe shell at the insertion end. The coil is preferably in close proximity to the rectum because the signal sensitivity of a small receive coil falls off sharply with distance. By necessity the receive coil width is no larger than about 2.5 cm, in order to be incorporated in probe shell 20, which is constructed in accordance with patient tolerance.

Receive coil 50 is incorporated in insertion end 30 of probe shell 20 for imaging the region of interest. FIG. 1B shows a cross-section view of probe shell 20 and relative placement of receive coil 50 being internal to probe shell 20. Referring again to FIG. 1, in order to obtain high resolution MR images, receive coil 50 is incorporated in the probe and this coil is placed as close as possible to the prostate.

Figure 2:
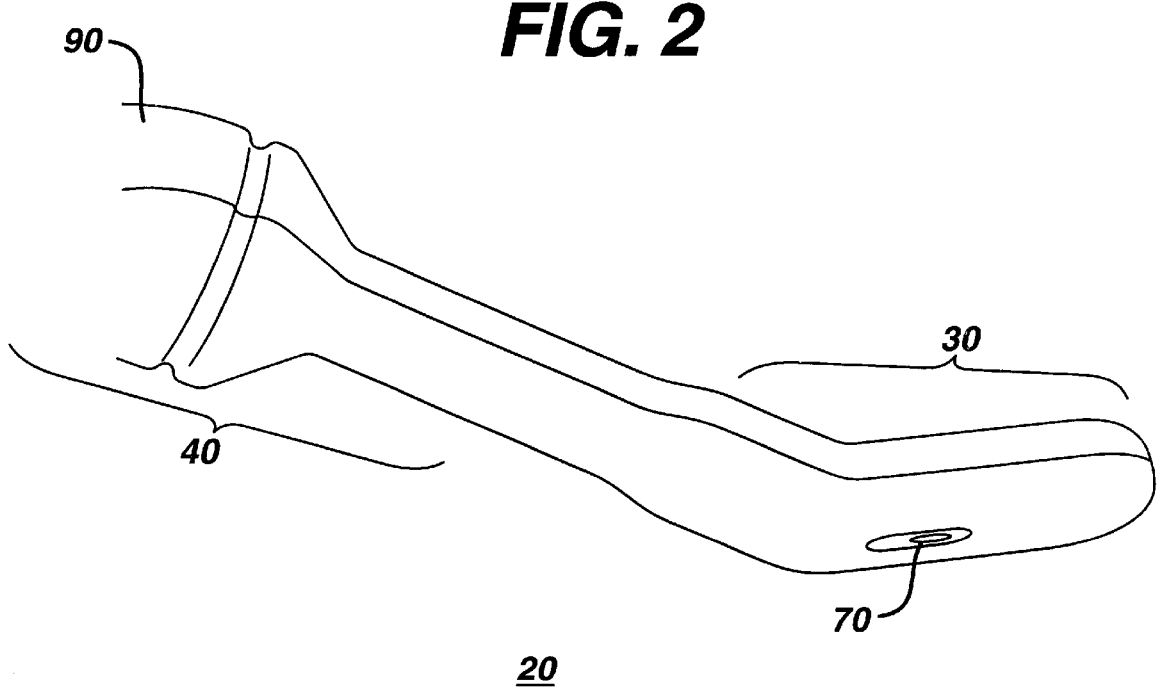
FIG. 2 shows a view of the insertion end of a probe shell of a type useful in the intracavity probe of FIG. 1.
Figure 3:
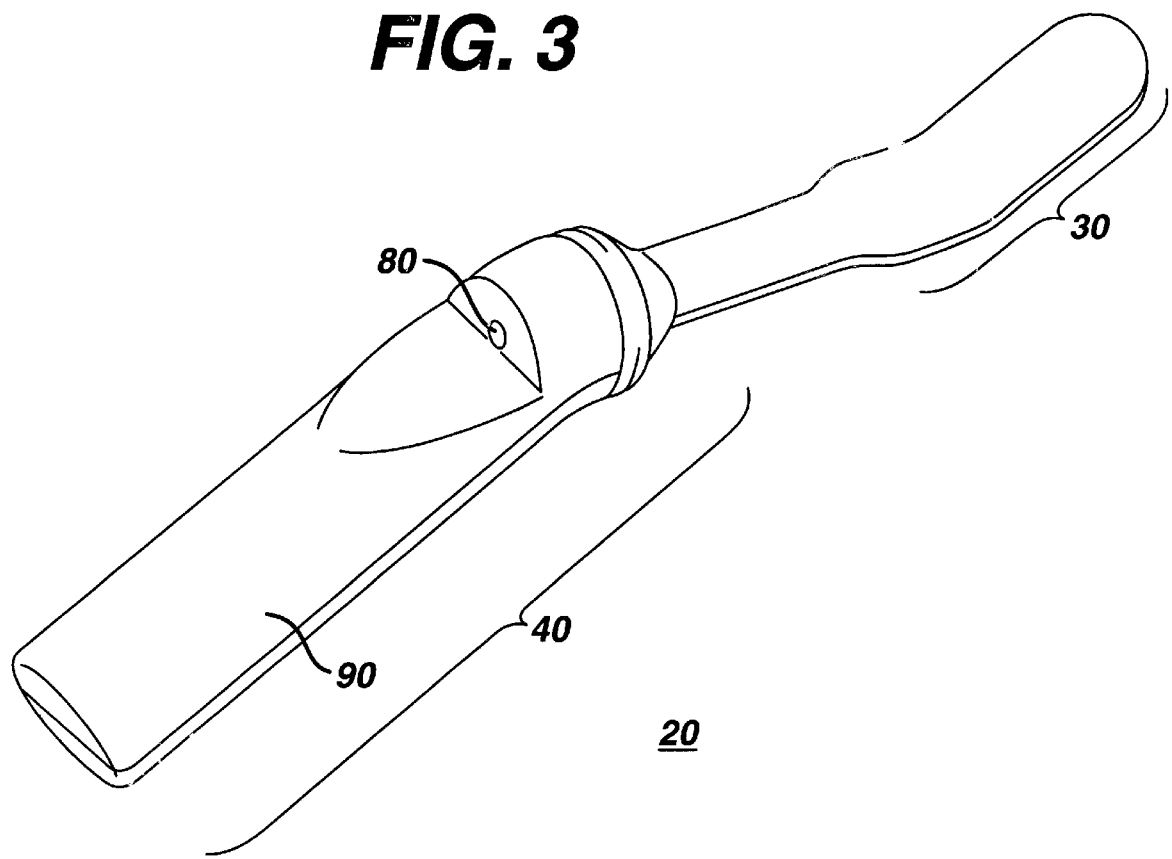
FIG. 3 shows a perspective view of a probe shell of a type useful in the intracavity probe of FIG. 1.
Figure 4:
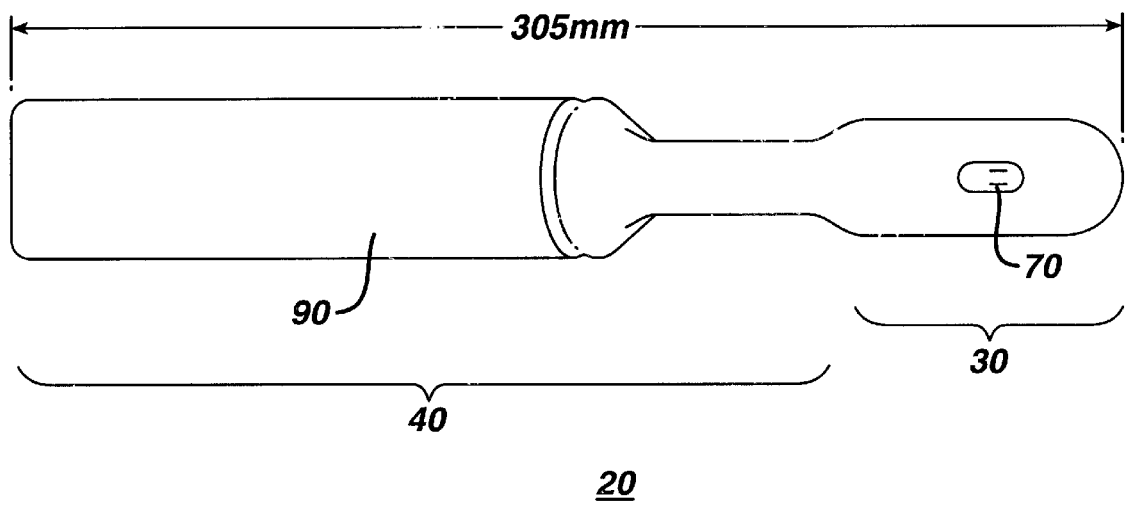
FIG. 4 shows a bottom view of a probe shell of a type useful in the intracavity probe of FIG. 1.

Referring again to FIG. 1, guide track 60 is incorporated in probe shell 20 and extends from insertion end 30 to a location on handle end 40 (not shown, see FIGS. 2 and 3) opposing the insertion end of the probe shell. FIG. 1A shows a cross-section view of probe shell 20 and guide track 60. Referring again to FIG. 1, guide track 60 is a channel or track adapted to guide a biopsy device, such as a biopsy needle, or a therapy device, such as a laser energy or brachytherapy device, to a region of interest. Hereinafter, the term "therapy device" shall refer to a biopsy or therapy device. FIG. 3 shows a top view of probe shell 20. Guide track entry 80 is at a location on handle 90 of the probe. The location of guide track entry 80 is shown on handle 90 for illustration purposes to be mid-way along the length of probe shell 20. Guide track entry 80 is adapted to receive a biopsy or therapy device and is coupled to guide track 60 in order to deliver the biopsy or therapy device to the insertion end of the probe. FIG. 4 shows a bottom view of probe shell 20 and shows guide track exit 70. FIG. 2 also shows guide track exit 70. Guide track exit 70 is located on insertion end 30 of probe shell 20, and is adapted to allow a biopsy or therapy device to pass from the probe to a region of interest, either for biopsy or therapy purposes. In another alternative embodiment, guide track 60 is used to deliver therapy such as laser energy or brachytherapy. It should be appreciated that locations of guide track entry and exit are shown as exemplary for prostate imaging and biopsy/therapy purposes, and such locations are varied for other applications such as cervical imaging or other rectal imaging purposes.

Figure 5:
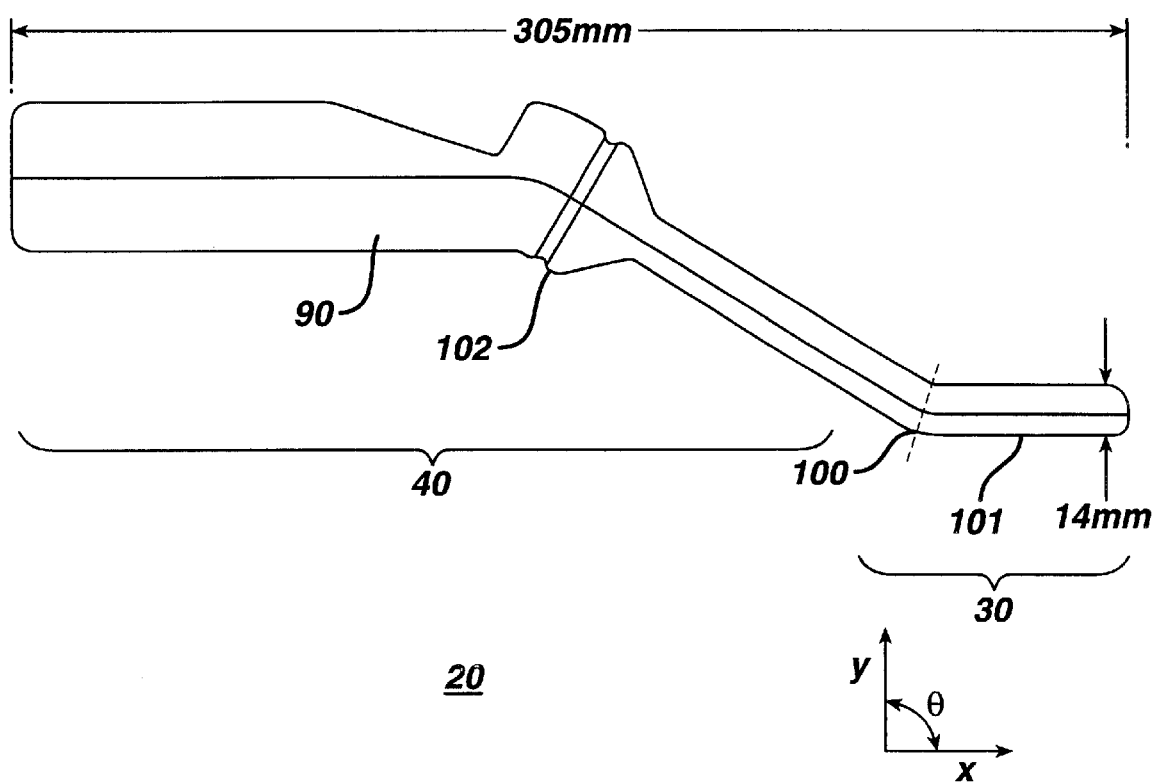
FIG. 5 shows a side view of a probe shell of a type useful in the intracavity probe of FIG. 1.
Figure 6:
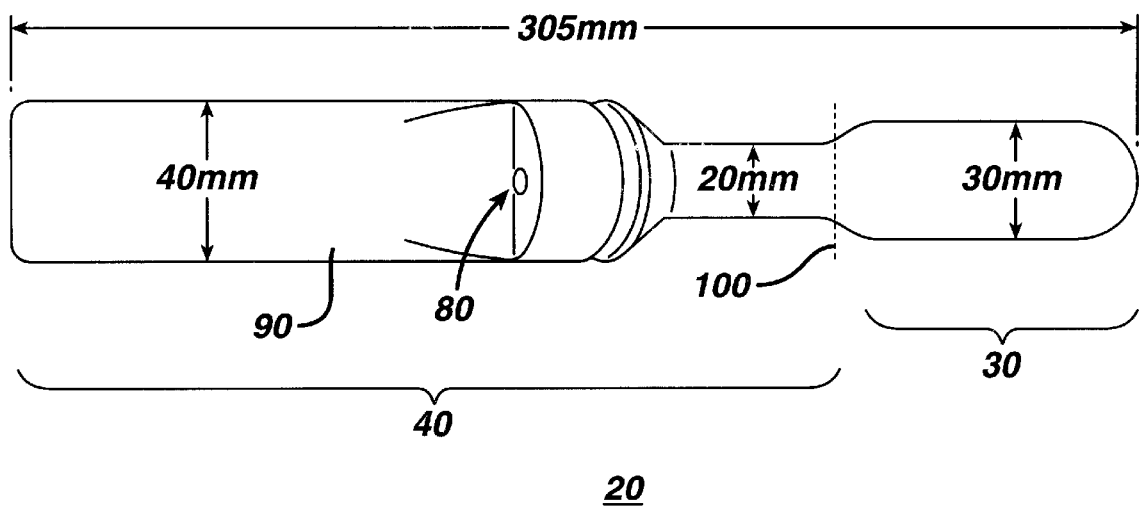
FIG. 6 shows a top view of a probe shell of a type useful in the intracavity probe of FIG. 1; and, FIG. 7 shows a view illustrating components useful in the intracavity probe of FIG. 1.

Referring to FIG. 5, a side view of probe shell 20 is shown. Probe shell 20 is a bent rod having a substantially hemispherical cross section, preferably of approximately 2.5 cm diameter. However, the substantially hemispherical shaped probe permits a diameter ranging from 2.5 cm to 3 cm (diameter of a hemisphere is illustrated in FIGS. 1A and 1B cross-section views as the length across the flat surface) that is tolerated by most patients. In an embodiment, the substantially hemispherical cross-section is at the insertion end of the probe. Referring to FIGS. 5 and 6, in an embodiment probe shell 20 is 305 mm in length. Bend 100 occurs at approximately 60–70 mm from insertion end 30 having an angle θ relative to the x-axis of approximately 30°. Bend 100 and flat surface 101 of the hemisphere allow the placement of a receive coil (not shown, see FIG. 1) of suitable dimensions adjacent to that surface. Flat surface 101 with the adjacent receive coil is brought up against the rectum wall so as to be in close proximity to the prostate as indicated in FIG. 1. A biopsy or therapy device, such as a biopsy needle, is guided through the probe to exit at the base of bend 100 (guide track exit 70 is shown in FIGS. 2 and 4), which gives advantageous access to all sectors of the prostate. Bend 100 allows for access to various sectors of the prostate and gives maximum positioning, movement and maneuverability of the probe inside the rectum. In tests involving cadavers, it was found that the shape of probe shell 20, as described in this embodiment provided additional maneuverability over that experienced using a straight cylindrical rod, the common design for ultrasound, or of a straight hemispherical rod. The comparison of these geometrical designs was done in 5 male cadavers and the bent hemispherical probe provided optimal access of the insertion end of the probe to various areas of the prostate. Bend 100 also permits less distortion of the rectum walls, and therefore, less patient discomfort, in order to bring the insertion end of the probe next to the prostate and to move the probe up and down along the rectum wall. Also advantageously, bend 100 and flat surface 101 permit the ability to bring therapy devices in close proximity to the prostate and over all the various prostate sectors. The location of bend 100 may vary depending on the application intended. The location is selected to accommodate a receive coil of suitable dimensions for a desired intracavity imaging application. Also illustrated in FIG. 5, bend 102 occurs at an angle θ relative to the x-axis of approximately 30° to provide maneuverability of the probe and permit insertion of biopsy or therapy devices into the probe. The dimensions shown in FIGS. 5 and 6 illustrate one embodiment, for exemplary purposes, suitable for MR imaging of a prostate as permitting adequate maneuverability and patient comfort. It can be appreciated that the location of bend 100 and other dimensions will vary for other intracavity imaging, such as cervical or other rectal applications.

Figure 7:
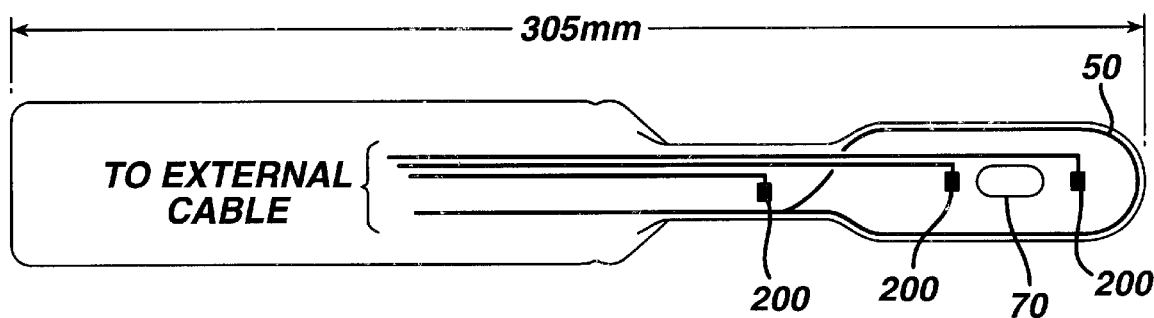

Several other devices may be advantageously incorporated into the probe. MR tracking coils are put in along guide track 60 so as to allow real time localization and registration of images with orientation and position of the probe. Thus, the biopsy volume position can be projected on the MR image in real time. The use of tracking coils is well known in the art of MR imaging. Referring to FIG. 7, in an embodiment, a set of three tracking coils measuring 2 mm in diameter and 4 mm in length are placed co-planar with receive coil 50 and guide track 60. In operation of an MRI system, a pulse sequence locates coordinates of each tracking coil and then prescribes a scan plane containing these coordinates. Guide track 60 is positioned within probe shell 20 so that it is contained within the plane defined by the three tracking coils. Thus, when the MR system acquires an image aligned with the tracking coils, the image contains the guide track. Since the location of the guide track is known with respect to the tracking coils, a graphical display of the therapy device, such as a biopsy needle, trajectory can be superimposed upon the image prior to actual insertion of the therapy device. In an embodiment, the tracking coils are 10-turn solenoids wound around glass capillary tubes containing a solution of $CuSO_4$. Tuning and matching capacitors and preamplifiers are also typically used. Handle 90 (shown in FIGS. 3–6) is used to incorporate such devices.

In an alternative embodiment, the intracavity probe described herein is adapted for ultrasound guided biopsy as it affords better access to the prostate with potentially less discomfort to the patient, as judged by morphometric measurements with male cadavers. The guide track shown in FIG. 1 is used to introduce other devices into the prostate, such as radio-frequency antennas for generalized prostate heating (for treatment of benign prostatic hyperplasia (BPH) and some forms of prostatitis). MR imaging would guide the placement of such probes and provide the critical requirement of monitoring temperature in the gland and adjacent tissues critical to maintenance of function.

Thus, a method for Magnetic Resonance Image (MRI) guided biopsy and therapy delivery of a region of interest proximal to a cavity of a patient, comprises the steps of positioning an intracavity probe, as described herein, in close proximity to the region of interest. Further steps include acquiring an MR image of the region of interest, guiding a biopsy or therapy device during MR image acquisition to acquire biopsy samples or deliver therapy to the region of interest, and, tracking the biopsy or therapy device during MR image acquisition.

While the preferred embodiments of the present invention have been shown and described herein, it will be obvious that such embodiments are provided by way of example only. Numerous variations, changes and substitutions will occur to those of skill in the art without departing from the invention herein. Accordingly, it is intended that the invention be limited only by the spirit and scope of the appended claims.

What is claimed is:

1. An insertable intracavity probe for use in Magnetic Resonance Imaging (MRI) and therapy of a region of interest proximal to a cavity, said probe comprising:

a substantially rigid probe shell for insertion into said cavity, said probe shell having an insertion end and a handle end opposing the insertion end, said probe shell being adapted to incorporate at least one device for imaging said region of interest, said probe shell further being adapted to incorporate at least one therapy device for use on said region of interest;

a receive coil being incorporated in the insertion end of the probe shell for use in imaging the region of interest; and, a guide track incorporated in said probe shell, said guide track being adapted to receive and guide the at least one therapy device through said insertion end to said region of interest.

2. The insertable intracavity probe of claim 1 wherein said insertion end of said probe shell has a substantially hemispherical shape having both a flat surface and a rounded surface, said flat surface being placed in close proximity with said region of interest.

3. The insertable intracavity probe of claim 2 wherein said probe shell has a bend at a location near said insertion end.

4. The insertable intracavity probe of claim 2 wherein said probe shell of hemispherical shape has a diameter of 2.5 cm.

5. The insertable intracavity probe of claim 1 further comprising at least one tracking coil for tracking a location of the insertion end and said guide track within said cavity.

6. The insertable intracavity probe of claim 1 wherein said therapy device is a biopsy needle.

7. The insertable intracavity probe of claim 1 wherein said therapy device is an ultrasound crystal.

8. The insertable intracavity probe of claim 1 wherein said guide track extends from the insertion end to a guide track entry on a location on said handle end of the probe shell.

9. An insertable intracavity probe for use in Magnetic Resonance Imaging (MRI) and therapy of a region of interest proximal to a cavity, said probe comprising:

a substantially rigid probe shell for insertion into said cavity, said probe shell having an insertion end and a handle end opposing the insertion end, said probe shell having a hemispherical shape at said insertion end, said hemispherical shape having a flat surface and a rounded surface, said probe shell having a bend near said insertion end of the probe shell;

at least one receive coil for use in imaging said region of interest, said at least one receive coil incorporated in the insertion end of said probe shell and adjacent to said flat surface of said probe shell;

a guide track located within said probe shell, said guide track extending from said insertion end of said probe to a guide track entry located on said handle end, said guide track receiving and guiding a therapy device to said region of interest during imaging of said region of interest; and, at least one tracking coil for tracking a location of the probe and said therapy device within said cavity.

10. The insertable intracavity probe of claim 9 wherein said probe shell of hemispherical shape has a diameter in a range of 2.5 cm to 3 cm.

11. An insertable intracavity probe for use in Magnetic Resonance Imaging (MRI) and biopsy of a region of interest proximal to a cavity, said probe comprising:

a substantially rigid probe shell for insertion into said cavity, said probe shell having an insertion end and a handle end opposing the insertion end, said probe shell having a hemispherical shape at said insertion end, said hemispherical shape having a flat surface and a rounded surface, said probe shell having a bend near said insertion end of the probe shell;

at least one receive coil for imaging said region of interest, said at least one receive coil incorporated in the insertion end of said probe shell and adjacent to said flat surface of said probe shell;

a biopsy device guide track located within said probe shell and extending from said insertion end of said probe to a guide track entry on said handle end, said biopsy device guide track receiving and guiding a biopsy device to said region of interest for acquiring samples of said region of interest for biopsy purposes during imaging of said region of interest; and, at least one tracking coil for tracking a location of the probe and said biopsy device within said cavity.

12. A method for Magnetic Resonance Image (MRI) guided biopsy and therapy delivery of a region of interest proximal to a cavity of a patient, comprising the steps of:

positioning an intracavity probe in close proximity to said region of interest, said intracavity probe being configured for insertion in said cavity and said intracavity probe being further configured to incorporate at least one device for imaging said region of interest and to incorporate at least one therapy device;

acquiring a MR image of said region of interest;

guiding a biopsy or therapy device during MR image acquisition to acquire biopsy samples or deliver therapy to said region of interest; and, tracking said biopsy or therapy device during MR image acquisition.

13. The method of claim 12, wherein said intracavity probe is substantially rigid, said intracavity probe having a shape and size selected for patient comfort.

14. The method of claim 12, where said region of interest is a prostate.

15. The method of claim 12, wherein said guiding step is performed through a guide track incorporated in said intracavity probe.

* * * * *